United States Patent [19]
Lafferty et al.

[11] Patent Number: 5,329,936
[45] Date of Patent: Jul. 19, 1994

[54] PORTABLE ARTHROSCOPE WITH PERISCOPE OPTICS

[75] Inventors: Michael Lafferty, Leucadia; Daniel Kline, Carlsbad; Charles S. Slemon, Encinitas, all of Calif.

[73] Assignee: Citation Medical Corporation, Reno, Nev.

[21] Appl. No.: 6,510

[22] Filed: Jan. 21, 1993

Related U.S. Application Data

[63] Continuation of Ser. No. 970,969, Nov. 3, 1992, which is a continuation of Ser. No. 814,418, Dec. 24, 1991, abandoned, which is a continuation-in-part of Ser. No. 650,066, Feb. 4, 1991, Pat. No. 5,188,093.

[51] Int. Cl.⁵ ............................................. A61B 1/06
[52] U.S. Cl. ..................................................... 128/6
[58] Field of Search .................................... 128/4, 6

[56] References Cited

U.S. PATENT DOCUMENTS

| | | | |
|---|---|---|---|
| 4,253,448 | 3/1981 | Terada | 128/4 |
| 4,589,404 | 5/1986 | Barath et al. | 128/6 |
| 4,590,923 | 5/1986 | Watanabe | 128/6 |
| 4,607,622 | 8/1986 | Fritch et al. | 128/6 |
| 4,620,769 | 11/1986 | Tsuno | 240/96.26 |
| 4,736,733 | 4/1988 | Adair | 128/6 |
| 4,754,328 | 6/1988 | Barath et al. | 358/98 |
| 4,755,873 | 7/1988 | Kobayashi | 358/98 |
| 4,762,120 | 8/1988 | Hussein | 128/6 |
| 4,782,819 | 11/1988 | Adair | 128/6 |
| 4,844,071 | 7/1989 | Chen et al. | 128/6 |
| 4,867,138 | 9/1989 | Kubota et al. | 128/6 |
| 4,920,961 | 5/1990 | Grossi et al. | 606/14 |
| 4,947,245 | 8/1990 | Ogawa et al. | 358/98 |
| 5,005,943 | 4/1991 | Fort | 350/96.26 |

FOREIGN PATENT DOCUMENTS

| | | |
|---|---|---|
| 0363118 | 4/1990 | European Pat. Off. |
| 0369936 | 5/1990 | European Pat. Off. |
| 0498114 | 8/1992 | European Pat. Off. |
| 9001028.0 | 5/1990 | Fed. Rep. of Germany |
| 60-226445 | 11/1985 | Japan |
| PCT/US84/01808 | 8/1984 | PCT Int'l Appl. |

*Primary Examiner*—Gene Mancene
*Assistant Examiner*—Nicholas D. Lucchesi
*Attorney, Agent, or Firm*—Nydegger & Associates

[57] ABSTRACT

A disposable arthroscope for examining the interior of a joint and for carrying out diagnostic and therapeutic procedures within the joint includes an elongated needle and a cap housing which has a base plate. The proximal end of the needle is mounted on the cap opposite the base plate, and the distal end of the needle extends outwardly from the cap. The needle is a hollow tube which surrounds an image guide and a bundle of illuminating fibers that extend through the tube. A lens is attached to the distal end of the image guide and is slightly angled relative to the longitudinal axis of the needle. The proximal ends of both the image guide and the bundle of illuminating fibers extend from the proximal end of the tube and through the cap for exposure at the surface of the base plate. The base plate of the disposable arthroscope is engageable with a camera and with a light source to position the camera in light communication with the image guide, and to position the light source in light communication with the bundle. With these engagements, the combination of disposable arthroscope, light source and camera generate a visual display of an object that is illuminated by the light source through the bundle of illuminating fibers.

21 Claims, 4 Drawing Sheets

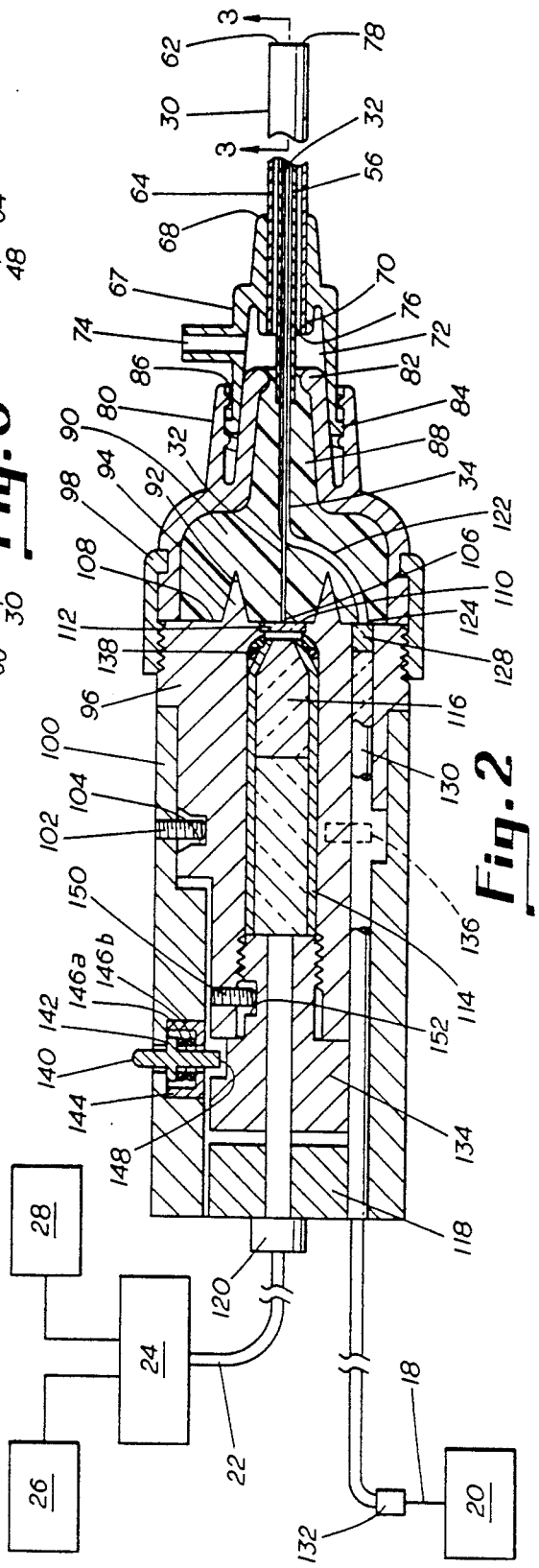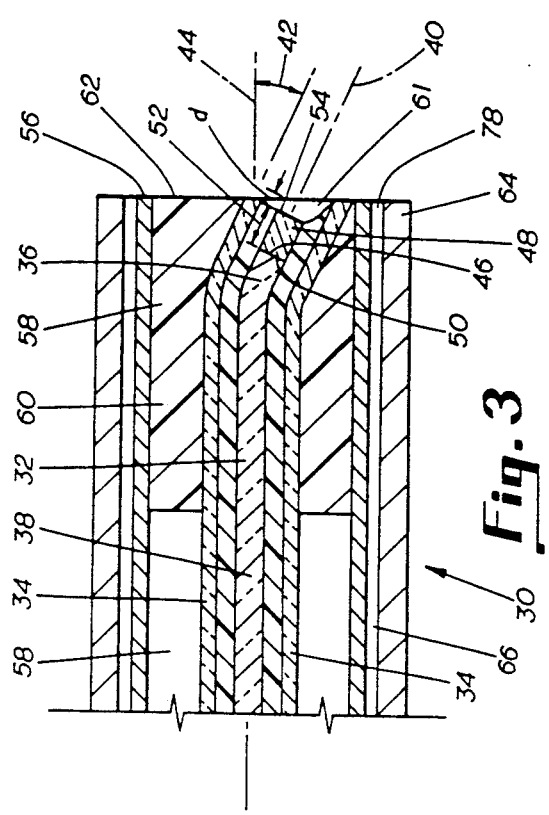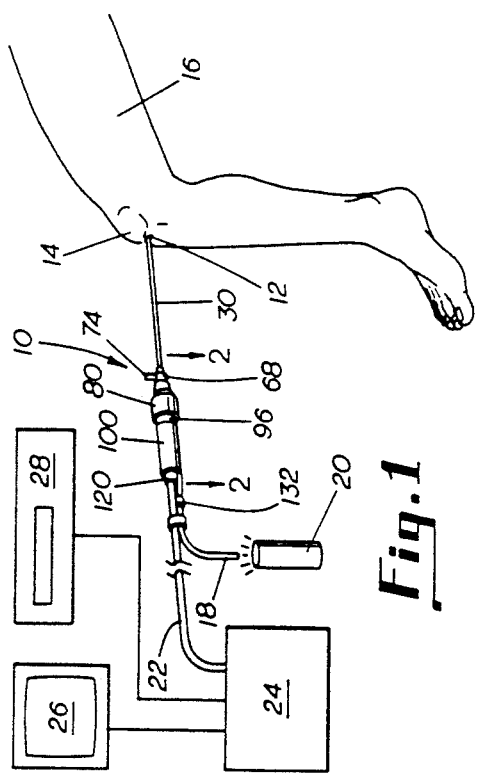

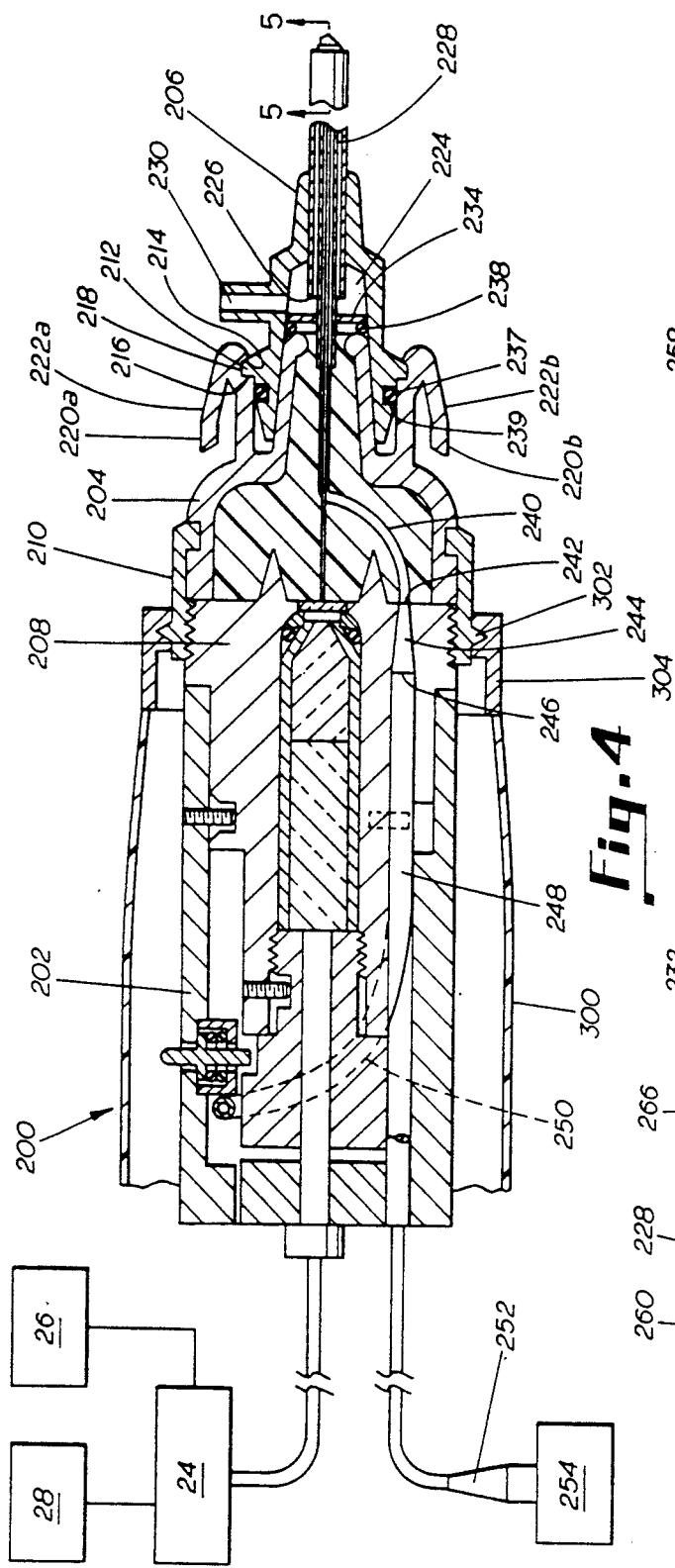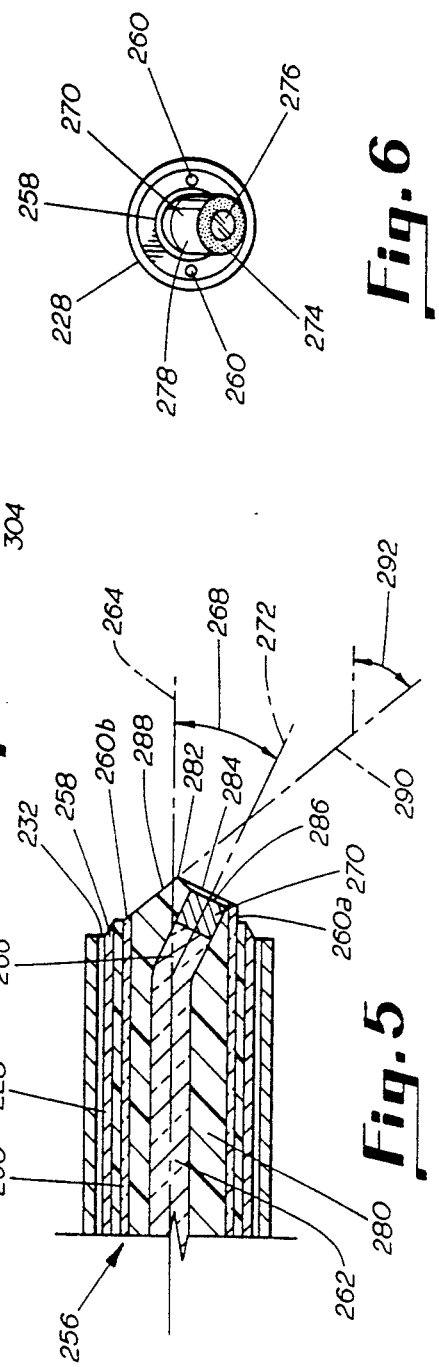

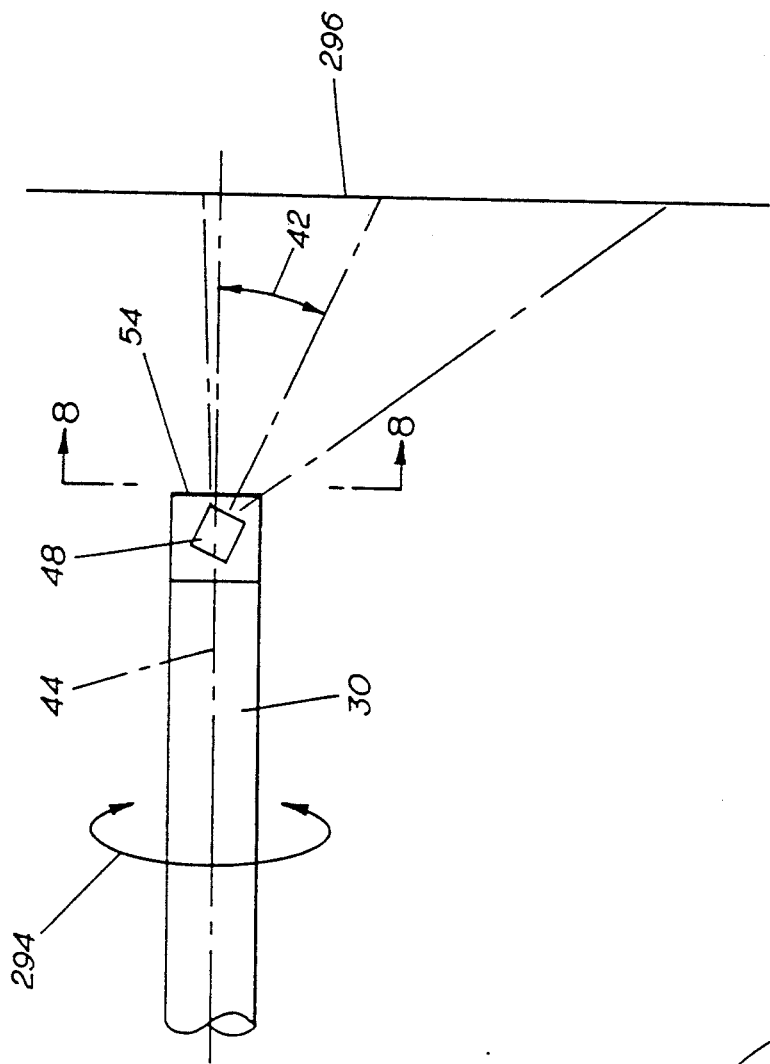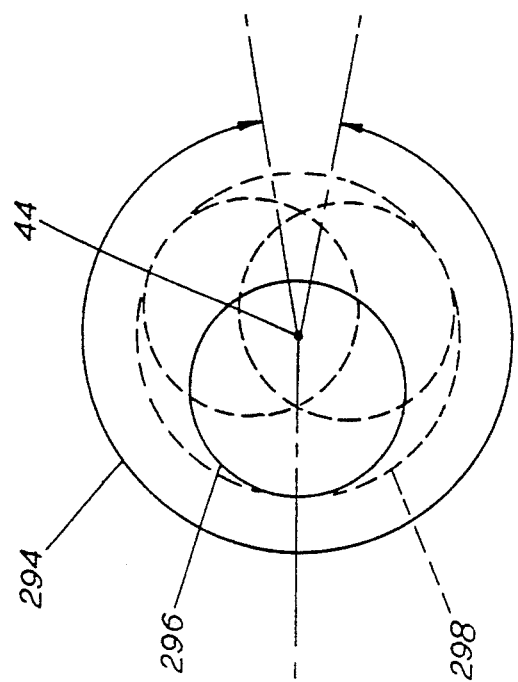

PORTABLE ARTHROSCOPE WITH PERISCOPE OPTICS

This is a continuation of application Ser. No. 07/970,969 filed on Nov. 3, 1992 now pending, which is a continuation of application Ser. No. 07/814,418 filed on Dec. 24, 1991, now abandoned, which is a continuation-in-part of application Ser. No. 07/650,066 filed on Feb. 4, 1991 which issued as U.S. Pat. No. 5,188,093.

FIELD OF THE INVENTION

The present invention relates generally to medical diagnostic devices. More particularly, the present invention relates to arthroscopes. The present invention particularly, though not exclusively, relates to hand-held portable arthroscopes for viewing a relatively large area within a body joint.

BACKGROUND OF THE INVENTION

In the area of medicine, modern surgical techniques have been developed for diagnosing and correcting damage to the interior structure of body parts, e.g., bone joints. One of these modern surgical techniques is arthroscopy, which can be used for examining the interior structure of a body joint, for example, a knee, in order to determine the extent of any damage to the joint. In other words, arthroscopy permits viewing the internal structure of a body joint without requiring conventional surgery on the joint. If required, relatively non-invasive corrective surgery can be performed in conjunction with arthroscopic examination techniques to repair joint damage which is discovered during the examination.

Arthroscopic examination typically involves inserting a probe into the joint to be examined. The probe has an imaging device attached to it, and the imaging device is in turn connected through the probe to a video display for generating a picture of the interior structure of the joint. Consequently, the operator of the arthroscope is able to view, real-time, the interior structure of the joint as the probe is inserted into the joint. By viewing the internal structure of the joint, a diagnosis of any damage to the joint can be made and appropriate treatment prescribed.

It is the case that existing arthroscopes require support equipment which is relatively large and bulky and which is typically permanently installed for use in an operating room. Consequently, these arthroscopes cannot be easily moved from one location to another, as may occasionally be required in a medical establishment. Furthermore, arthroscopes which require sizable support equipment are ordinarily expensive devices, and their relatively high cost can make arthroscopic examination cost prohibitive for some patients. The present invention recognizes that an arthroscope need not require large and expensive support equipment and that there is a need to provide an arthroscope which can be used in a Doctor's office for diagnosis of a joint injury. Further, there is a recognized need to provide an arthroscope with a sufficiently small disposable probe so that only a local anesthetic is necessary.

Additionally, the probes of existing arthroscopes are typically reusable devices and must accordingly be sterilized before each use, in order to eliminate the possibility of infecting the arthroscopy patient with a contaminated probe. Unfortunately, the possibility remains that a reusable probe may not be effectively sterilized and can accordingly remain septic, or that a properly sterilized probe could become septic in the time period between sterilization and use of the probe. The present invention recognizes that an arthroscope can be provided which uses a non-reusable probe to substantially reduce the likelihood of transmitting infections.

In addition to the above considerations, it is also desirable for the arthroscope to have a relatively wide field of view when the probe of the arthroscope is positioned within the joint. This is in order to maximize the size of the internal body area which the arthroscope operator can examine. Providing a wide field of view simply by enlarging the lens of the arthroscope, however, would be counterproductive since the introduction of a larger lens would require a larger entry site into the knee. A larger entry site, however, is to be avoided. Accordingly, it is desirable that the arthroscope be capable of viewing a relatively large area within a joint, without requiring the use of a comparatively large arthroscope lens.

It is accordingly an object of the present invention to provide an arthroscope which is portable and hand-held. It is a further object of the present invention to provide an arthroscope which has a disposable probe that is insertable into a body joint for generating a real-time picture of the joint. It is also an object of the present invention to provide an arthroscope which can view a relatively large portion of the internal structure of a joint. Finally, it is an object of the present invention to provide an arthroscope which is relatively inexpensive to manufacture and comparatively easy and cost-effective to use.

SUMMARY

A portable diagnostic arthroscope has a hand-held generally cylindrical hollow camera assembly and a disposable scope assembly removably attached to the distal end of the camera assembly. The disposable scope assembly can be rotated relative to the camera assembly. Further, an elongated probe is rotatably attached to the disposable scope assembly.

More specifically, the probe includes a hollow tubular steel cannula which is mounted on a base assembly. The cannula extends beyond the distal end of the base assembly, and the base assembly is rotatably engaged with the scope assembly, so that the base assembly, with its cannula, can be rotated relative to the score assembly. The cannula itself has an open distal end and an open proximal end, so fluid can be introduced into the base assembly and directed through the cannula to bathe the internal joint structure.

In accordance with the present invention, a cylindrically-shaped GRIN rod is attached to the end of a scope needle which is slidably introduced through the cannula to position the GRIN rod inside the cannula near the cannula's open distal end. Light which is reflected by the interior structure of the joint enters the distal base of the cylindrically-shaped GRIN rod and is focussed by the GRIN rod onto the GRIN rod's proximal base.

To transfer the light back through the scope needle, the proximal base of the GRIN rod is attached to the distal end of a fiber optic image guide. This image guide extends through the scope needle which is part of the scope assembly. Light which enters the distal base of the GRIN rod is focussed by the GRIN rod onto the image guide. Importantly, the image guide is bent near its distal portion to form an angle of about twenty-five (25) degrees between the distal portion of the image guide and the axis of the probe. Consequently, the axis of the GRIN rod, which is attached to the distal end of the image guide, is not parallel to the axis of the probe. Accordingly, when the scope assembly is turned to rotate the image guide about its axis, the distal base of the GRIN rod is moved through a donut-shaped swath which enables the GRIN rod to scan a relatively large area of the internal structure of the joint.

The image guide is optically joined to focussing optics which are mounted in the camera assembly. These focussing optics are axially movable within the housing for focussing the image from the image guide onto the camera head in the camera assembly. Thus, the focussing optics are optically joined with a camera head which is mounted in the camera assembly and which is electrically connected to a camera control unit external to the arthroscope. As envisioned by the present invention, the camera control unit can control a CRT or other visual display device to display the image of the internal structure of the joint.

Also, to illuminate the interior structure of the joint, a plurality of optical illumination fibers are mounted within the scope needle next to the image guide. These illumination fibers extend through the scope assembly and are joined with a first end of an optical cable that is mounted inside the camera assembly. In accordance with the present invention, the second end of the optical cable can be irradiated with light from a quartz halogen lamp or other suitable light source which can be located either in the scope assembly or the camera assembly, or located externally to the camera assembly. Thus, light from the lamp can be transmitted through the optical cable and illumination fibers to illuminate the internal structure of the joint.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a perspective view of the novel portable arthroscope of the present invention, seen in its intended environment;

FIG. 2 is a partial cross-sectional view of the novel portable arthroscope of the present invention, as seen along the line 2—2 in FIG. 1;

FIG. 3 is an enlarged cross-sectional view of the distal end of the probe of the novel portable arthroscope of the present invention shown in FIG. 2; as seen along the line 3—3 in FIG. 2;

FIG. 4 is a partial cross-sectional view of an alternate embodiment of the present arthroscope, as would be seen along the line 2—2 in FIG. 1;

FIG. 5 is an enlarged cross-sectional view of the distal end of the probe of the arthroscope shown in FIG. 4, as seen along the line 5—5 in FIG. 4;

FIG. 6 is an end view of the probe of the present invention;

FIG. 7 is a schematic view of the viewing area of the GRIN rod of the present invention;

FIG. 8 is a schematic view of the viewing area of the GRIN rod of the present invention, as seen in the direction of arrow 8 in FIG. 7;

DESCRIPTION OF THE PREFERRED EMBODIMENT

Figure 9A:
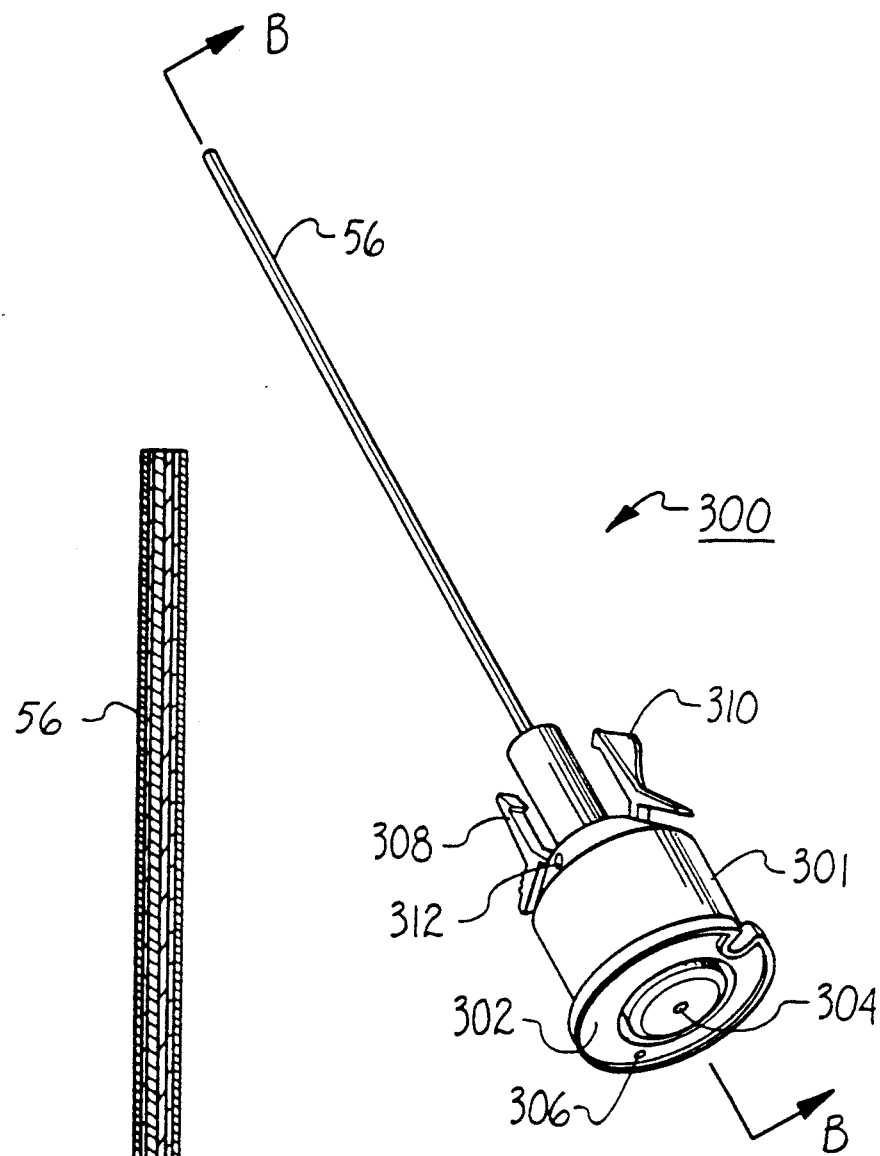
FIG. 9A is a perspective view of the disposable arthroscope of the present invention.

Referring initially to FIG. 1, a portable hand-held arthroscope is shown, generally designated 10. As shown, a portion of arthroscope 10 is inserted at an entry site 12 into a knee 14 of patient 16 to examine the internal structure of the knee 14. Arthroscope 10 is in light communication via optical illumination line 18 to a quartz halogen lamp 20. While the present invention envisions use of a lamp 20 which is a quartz halogen lamp for economy, it is to be understood that lamp 20 may alternatively be any other suitable type of light source well known in the art, e.g., metal halide.

FIG. 1 also shows that arthroscope 10 is electrically connected via line 22 to a camera control unit 24. Camera control unit 24 can in turn be electrically connected to a cathode ray tube (CRT) 26 and a video camera recorder (VCR) 28, as shown in FIG. 1, for respectively displaying and recording a video image of the internal structure of knee 14.

Now referring to FIGS. 2 and 3, the details of arthroscope 10 can be seen. As shown in FIG. 2, arthroscope 10 includes a probe 30 which is insertable into knee 14 (shown in FIG. 1). FIG. 3 shows that probe 30 includes a scope needle 56 which has an optical fiber image guide 32 which is coaxial with the scope needle 56 for most of its length. FIG. 3 further shows that probe 30 includes a plurality of optical illuminating fibers 34 which are positioned in the scope needle 56 around image guide 32. Preferably, both image guide 32 and illuminating fibers 34 are optical fibers which have relatively large numerical apertures (NA). Additionally, although there is no limitation on length, image guide 32 is preferably short, i.e., the length of image guide 32 is preferably less than about eight (8) inches.

As shown in FIG. 3, the distal segment 36 of image guide 32 is not collinear with the proximal segment 38 of image guide 32. More particularly, image guide 32 is bent so that the axis 40 of distal segment 36 forms an angle 42 of about twenty five (25) degrees relative to the axis 44 of proximal segment 38 and probe 30. Image guide 32 is bent during the manufacturing process to the shape substantially as shown in FIG. 3. For purposes of the present invention, image guide 32 is of a type well known in the pertinent art which comprises a single rod having a plurality of pixels (e.g. 10,000 pixels).

Still referring to FIG. 3, the proximal end 46 of a cylindrical gradient refractive index (GRIN) lens 48 is bonded to the distal end 50 of image guide 32. Preferably, GRIN lens 48 is the type of internally-refractive lens made of thallium-doped glass manufactured by Nippon Sheet Glass. In accordance with the present invention, the length 52 of GRIN lens 48 establishes the focussing characteristics of GRIN lens 48 as appropriate for the particular application of arthroscope 10.

Importantly, as shown in FIG. 3, the distal end 54 of GRIN lens 48 defines a viewing window which is offset, i.e., not perpendicular to, axis 44 of probe 30 as a consequence of the bend formed in image guide 32. Stated differently, the axis 40 of distal segment 36 (and, hence, the axis of GRIN lens 48) is not parallel to the axis 44 of proximal segment 38 of image guide 32. Accordingly, when probe 30 (and, hence, image guide 32) is rotated in a manner to be subsequently disclosed, distal end 54 of GRIN lens 48 rotates through (and collects light from) a relatively large area. Consequently, it may be appreciated that by rotating probe 30, arthroscope 10 can examine a relatively large area of the internal structure of knee 14 (shown in FIG. 1).

Continuing with the description of structure shown in FIG. 3, probe 30 is shown to include a hollow scope needle 56 which has a lumen 58. As shown, needle 56 is positioned in a surrounding relationship with image guide 32 and illuminating fibers 34. Needle 56 is preferably a hollow 16-gauge stainless steel tube, and image guide 32 and illuminating fibers 34 are positioned in the lumen 58 of needle 56. The portion of lumen 58 which surrounds image guide 32 and illuminating fibers 34 is filled with an opaque epoxy material 60, to cushion and support image guide 32 and illuminating fibers 34 and to shield unwanted light from entering the image guide 32. It is to be appreciated in reference to FIG. 3 that end 62 of epoxy material 60 is preferably polished. As shown, distal end 54 of GRIN lens 48 is recessed a distance d from end 62. In the preferred embodiment, distance d is approximately five thousandths of an inch. Additionally, FIG. 3 shows that the portions of lumen 58 which is proximal to GRIN lens 48 is left open and is not filled with epoxy 60 in order to contain damage in the event probe 30 became inadvertently bent.

FIG. 3 further shows that probe 30 includes a 14-gauge hollow stainless steel cannula 64 which is positioned in a surrounding relationship to needle 56 with a passageway 66 between cannula 64 and needle 56 through which fluid can be infused. Though not shown in FIG. 3, it is to be appreciated that GRIN lens 48 can be protected from getting epoxy on the face of the GRIN lens 48 by placing a polymide tubing around the GRIN lens 48. Further, this polymide tubing will assist in protecting GRIN lens 48 from adverse affects of thermal expansion.

Referring back to FIG. 2, cannula 64 of probe 30 is shown attached to a disposable injection-molded hub 67 near proximal end 70 of probe 30 to establish cannula assembly 68. Cannula assembly 68 is formed with a chamber 72, and fluid can be pumped into chamber 72 through fluid port 74 from a fluid source (not shown). Fluid in chamber 72 can enter open end 76 of cannula 64 and pass through passageway 66. This fluid can subsequently be flushed out of open end 78 (shown in FIG. 3) of cannula 64 to bathe the internal structure of knee 14 to provide a clear viewing field when probe 30 is inserted into knee 14.

Cannula assembly 68 is rotationally engageable with a disposable hollow injection-molded scope assembly 80, as shown in FIG. 2. More specifically, bulb portion 82 of scope assembly 80 extends into cannula assembly 68, and luer ears 84 of cannula assembly 66 can be threadably engaged with luer fitting 86 of scope assembly 80. As shown in FIG. 2, scope assembly 80 has a chamber 88 which is filled with a resilient epoxy material 90. Epoxy material 90 is in turn formed with key guides 92. Key guides 92 are configured for engaging the keys 94 which protrude from a front tube 96. More specifically, keys 94 of front tube 96 engage key guides 92 of epoxy material 90 to establish a predetermined orientation of front tube 96 relative to epoxy material 90. This predetermined orientation ensures that the optical components in scope assembly 80 are properly aligned with associated optical components in front tube 96 when scope assembly 80 is joined to front tube 96.

To hold scope assembly 80 against front tube 96, arthroscope 10 includes a retainer ring 98 which is slidably engaged with scope assembly 80 and threadably engageable with front tube 96 to removably connect scope assembly 80 to front tube 96. Furthermore, as shown in FIG. 2, front tube 96 is rotatably positioned in a camera assembly 100 and is held axially stationary with camera assembly 100 by retaining screw 102. More particularly, retaining screw 102 is threadably engaged with camera assembly 100 and extends into a groove 104 which circumscribes front tube 96. Consequently, front tube 96 can be rotated relative to housing 100.

In describing the optical path through arthroscope 10, reference is made to FIG. 2, which shows that image guide 32 extends through epoxy material 90 of scope assembly 80. As shown, end 106 of image guide 32 is substantially coplanar with surface 108 of epoxy material 90. In accordance with the present invention, surface 108 is polished to a smooth finish to establish an image plane 110.

Light from image guide 32 which passes through image plane 110 impinges upon a transparent sapphire window 112. It is to be appreciated in reference to FIG. 2, that window 112 is fixedly mounted on front tube 96. It is to be further appreciated that window 112 is made of a material, i.e., sapphire, that is easy to clean yet hard to scratch. Additionally, an optics base 114 is slidingly positioned in front tube 96. Optics base 114 holds a focussing optic 116 which is in light communication with sapphire window 112. Thus, light which has passed through sapphire window 112 can enter focussing optic 116. Preferably, focussing optic 116 magnifies light from sapphire window 112 approximately seven times (7×) and focuses the light onto a camera head 118 which is also mounted in optics base 114. In the preferred embodiment, camera head 118 is a charged coupled device (CCD).

In accordance with the present invention, camera head 118 converts the light image from focussing optics 116 to an electrical signal representative of the internal structure of knee 14. This electrical signal is coupled into an appropriate electrical connector 120. As disclosed above, the electrical signal is conducted via line 22 to CCU 24 for further processing.

In describing the structure of arthroscope 10 which is used for illuminating the interior of knee 14, reference is made to FIG. 2, which shows that illuminating fibers 34 extend through epoxy material 90 in a fiber bundle 122 to end 108 of epoxy material 90. As shown, when the cap 80 is engaged with front tube 96, end 124 of fiber bundle 122 is juxtaposed with an illumination GRIN rod 128 which is, in turn, connected to optical continuation fiber 130. Continuation fiber 130 is in turn coupled to an optical connector 132, and optical connector 132 is in light communication with lamp 20 through optical line 18.

As disclosed above, arthroscope 10 incorporates a periscope feature wherein scope assembly 80 can be rotated relative to camera assembly 100 to rotate probe 30, and to selectively focus the image present on image plane 110. More specifically, by rotating probe 30, distal base 54 of GRIN lens 48 rotates through a donut-shaped swath for viewing a comparatively large area within knee 14. Also, the present invention provides a capability for focussing the image present on image plane 110 when scope assembly 80 is rotated relative to camera assembly 100.

In describing the details of the structure of arthroscope 10 for rotating probe 30 and for focussing the light image which is present on image plane 110, reference is made to FIG. 2. Recall that retainer ring 98 holds scope assembly 80 onto front tube 96, and that front tube 96 can be rotated within camera assembly 100. If desired, to limit the rotational motion of front tube 96 relative to camera assembly 100 to 170° in both the clockwise and counter-clockwise directions, stop screws (only stop screw 136 shown in phantom in FIG. 2), can be threadably engaged with front tube 96 to contact retaining screw 102.

In accordance with the present invention, a focussing ring 134 is threadably engaged with front tube 96 and abuts optics base 114, and a resilient annular O-ring 138 is positioned between front tube 96 and optics base 114 to urge optics base 114 against focussing ring 134. Focussing ring 134 can be operated to urge against optics base 114 to move optics base 114 as appropriate for focussing the image from image plane 110 onto the camera head CCD 118.

More particularly, as shown in FIG. 2, a button 140 is reciprocally mounted in camera assembly 100. As shown, button 140 has a collar 142 which can abut camera assembly 100 to retain button 140 in camera assembly 100. Furthermore, a flange 144 is fixedly attached to camera assembly 100, and two biasing O-rings 146 a,b are positioned between flange 144 and collar 142 of button 140 to bias collar 142 of button 140 against camera assembly 100 and provide a water seal. When button 140 is depressed, end 148 of button 140 contacts focussing ring 134 to hold ring 134 stationary relative to camera assembly 100. Thus, with button 140 depressed, when scope assembly 80 (and, hence, front tube 96) is rotated relative to camera assembly 100 scope assembly 80 is also rotated relative to focussing ring 134, which is being held stationary relative to camera assembly 100 by button 140. Consequently, stationary focussing ring 134, which is threadably engaged with rotating front tube 96, urges against optics base 114 to cause optics base 114 to move axially relative to front tube 96, scope assembly 80, and hence, image plane 110. When optics base 114 (and, hence, optic 116) is appropriately moved relative to image plane 110, the optical image present on image plane 110 can be focused.

It will be appreciated in reference to the discussion above that when scope assembly 80 is rotated clockwise relative to camera assembly 100 and button 140 is depressed, ring 134 urges optics base 114 distally relative to image plane 110 (i.e., toward the right in FIG. 2). On the other hand, when scope assembly 80 is rotated counterclockwise relative to camera assembly 100 and button 140 is depressed, resilient O-ring 138 urges optics base 114 proximally relative to image plane 110 (i.e., toward the left in FIG. 2). Consequently, as optics base 114 is moved axially relative to scope assembly 80, the focussing optics 116 which are mounted in optics base 114 also move axially relative to scope assembly 80 (and, hence, image plane 110) to focus the image present on image plane 110.

On the other hand, when scope assembly 80 (and, hence, front tube 96) is rotated relative to camera assembly 100, and button 140 is not depressed, focussing ring 134 is not held stationary relative to optics base 114. Consequently, optics base 114 is not moved axially relative to image plane 110, and the focus of the image from image plane 110 does not change. Importantly, however, image guide 32 is rotated relative to camera assembly 100, so that the area "viewed" by GRIN lens 48 rotates within knee 14 through a relatively wide swath.

Finally, FIG. 2 shows that a screw 150 is threadably engaged with front tube 96. Furthermore, screw 150 extends into a slot 152 that is formed in focussing ring 134. It will be appreciated that the widths of screw 150 and slot 152 establish the range of axial travel of ring 134 relative to front tube 96. In the preferred embodiment ring 134 can travel axially relative to front tube 96 a distance of about twenty (20) thousandths of an inch.

Now referring to FIGS. 4 and 5, an alternate embodiment of the novel arthroscope of the present invention is shown and generally designated 200. It is to be understood that arthroscope 200 is in all essential respects identical with arthroscope 10, with the exceptions disclosed below. More particularly, arthroscope 200 includes a camera assembly 202, a scope assembly 204, and a cannula assembly 206. As shown, scope assembly 204 is removably attached to a front tube 208 by retainer ring 210, and front tube 208 is in turn rotatably mounted in camera assembly 202.

FIG. 4 shows that cannula assembly 206 is rotatably attached to scope assembly 204, and that cannula assembly 206 can be removed from scope assembly 204. More specifically, cannula assembly 206 includes an abutment 212 and scope assembly 204 includes a detent 214 and a stop 216 which together establish an annular space 218. As shown in reference to FIG. 4, cannula assembly 206 can be urged proximally toward scope assembly 204 to snappingly engage abutment 212 with space 218 between detent 214 and stop 216. In accordance with the present invention, when abutment 212 is engaged with space 218, cannula assembly 206 can be rotated relative to scope assembly 204. To disengage cannula assembly 206 and scope assembly 204, ends 220a, b of respective arms 222a, b of scope assembly 204 are urged radially inwardly, and cannula assembly 206 is pulled distally away from scope assembly 204.

As further shown in FIG. 4, cannula base assembly 206 includes a reservoir 224 which is in fluid communication with the open proximal end 226 of a cannula 228. As shown, a fluid line 230 can be attached to cannula assembly 206 in fluid communication with reservoir 224, for flushing fluid into proximal end 226 of cannula 228 and out of the distal end 232 of cannula 228 (shown in FIG. 5). To prevent fluid from cannula 2218 from spraying the operator of arthroscope 200 when cannula assembly 206 is detached from scope assembly 204, a pierceable fluid seal 234 can be positioned in reservoir 224 substantially as shown. Scope needle 56, when inserted into cannula 228, will pierce through the fluid seal 234. Also, a retainer ring 238 is bonded to cannula assembly 206 to retain fluid seal 234 within reservoir 224. Furthermore, an annular O-ring 237 is positioned in groove 239 of cannula assembly 206 to provide an additional seal between reservoir 224 and the operator of arthroscope 10.

Still referring to FIG. 4, arthroscope 200 is shown to include a plurality of optical illumination fibers which are grouped in a fiber bundle 240. As shown, fiber bundle 240 extends through scope assembly 204 and is optically joined to the distal base 242 of a fiber optic taper 244. Taper 244 is shaped as a right circular conical frustum, and the distal base 242 of taper 244 has approximately half the area of the proximal base 246 of taper 244. Proximal base 246 of taper 244 is joined to an optical transmission fiber 248. It will be appreciated by the skilled artisan that taper 244 directs flight from transmission fiber 248 into fiber bundle 240, to maximize the amount of light transmitted through fiber bundle 240 for illuminating the internal structure of the knee.

Preferably, optical transmission fiber bundle 240 has a higher numerical aperture than do the illumination fibers which constitute fiber bundle 248. In any case, the numerical apertures for both bundle 240 and 248 should be as high as possible. Additionally, as shown in FIG. 4, transmission fiber 248 includes a slack loop segment 250 to compensate for movement of transmission fiber bundle 248 when scope assembly 204 is rotated relative to camera assembly 202.

A second optical fiber taper 252 is shown in FIG. 4 for optically connecting transmission fiber bundle 248 to a light source 254. Taper 252 maximizes the light from light source 254 which can be transmitted through transmission fiber 248.

Now referring to FIG. 5, the details of the distal end of arthroscope 200 can be seen to include a probe, generally designated 256. Probe 256 includes cannula 228. Additionally, probe 256 includes a steel needle 258, a plurality of optical illumination fibers 260, and an optical fiber image guide 262. It is to be understood that needle 258 and illumination fibers 260 are substantially identical to the needle 56, fibers 34, and image guide 32, respectively, disclosed for arthroscope 10.

As shown, image guide 262 substantially defines a longitudinal axis 264, and the distal segment 266 of image guide 262 is bent at an angle 268 relative to image guide 262. Preferably, angle 268 is about twenty five (25) degrees. FIG. 5 also shows that a cylindrical GRIN rod 270 is attached to the distal end of image guide 266. Consequently, the axis 272 of GRIN rod 270 is oriented at an angle 268 to the axis 264 of image guide 262.

Referring briefly to FIG. 6, an iris 274 is shown at the distal base of GRIN rod 270. Preferably, iris 274 is an opaque material which is deposited onto GRIN rod 270. As shown in FIG. 6, iris 274 includes an aperture 276 through which light can pass. If desired, the side surface 278 of GRIN rod 270 can also be coated with an opaque material, to reduce the amount of stray light which can enter GRIN rod 270 through surface 278 and thereby interfere with image of the interior of the body surface under examination.

Referring back to FIG. 5, an epoxy material 280 is shown disposed within needle 258 in a surrounding relationship to image guide 262 and illumination fibers 260. Distal surface 282 of epoxy material 280 is preferably polished, and, as shown in FIG. 5, distal surface 282 is contoured to optimize light transmission out of illumination fibers 260 and into image guide 262. More specifically, portion 284 of surface 282 is substantially parallel to distal base 286 of GRIN rod 270, to optimize light transmission into distal base 286. For increasing the illumination of the interior body structure under examination, portion 288 of surface 282 is oriented for maximizing the refractive angle of light which exits illumination fiber 260b. As shown, portion 288 of distal surface 282 of epoxy material 280 lies in a plane 290 that forms an angle 292 of about fifty degrees with the axis 264 of image guide 262.

FIG. 4 also shows that a flexible protective sheath 300 can be provided which maintains the sterility of the arthroscope 10 during its use. Specifically, a raised ring 302 is formed on the retainer ring 210 and a slip ring 304 is engaged with the raised ring 302. The sheath 300, which is attached to slip ring 304 is then draped over the camera assembly 202 and any other reusable components of the arthroscope 10 which are likely to be septic.

Accordingly, the sterilized portions of arthroscope 10, which are also disposable can be joined with the reusable camera assembly 202 which is covered by the sheath 300.

Figure 9B:
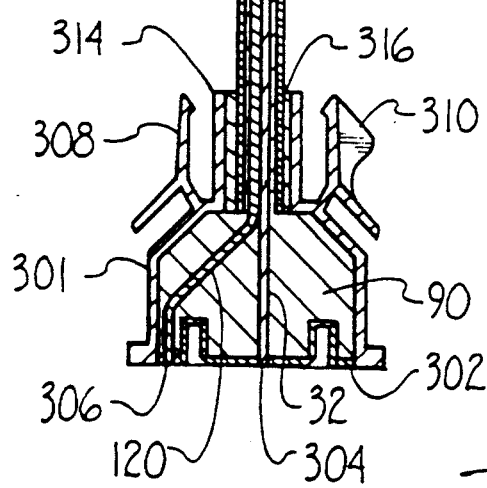
FIG. 9B is a cross-sectional view of the disposable arthroscope as seen along the line B—B in FIG. 9A.

Another specific embodiment for the disposable arthroscope of the present invention is shown in FIGS. 9A and 9B and is generally designated 400. For this embodiment, as with the other embodiments for the arthroscope previously disclosed, the needle 56 is a hollow tube which surrounds portions of both the image guide 32 and the fiber bundle 122. As before, the fiber bundle 122 contains the illuminating optical fibers.

The proximal end of needle 56 is mounted on a housing cap 401 and the distal end of the elongated needle 56 extends outwardly from the cap 401. As seen in both FIGS. 9A and 9B, arthroscope 400 also includes a base plate 402 which is attached to cap 401 opposite from where the needle 56 is joined to the cap 401. Further, base plate 402 is formed with an aperture 404 which is centrally located on the base plate 402, and with an aperture 406 which is distanced from the aperture 404 and located near the periphery of base plate 402. It will also be seen in the Figures that the cap 401 is formed with a pair of clips, 408 and 410, which are mounted on the cap 401 and which are diametrically opposed to each other relative to the needle 56. As intended for the present invention, the clips 408 and 410 are used to engage the arthroscope 400 with the cannula assembly 206.

The specific cooperation of structure for the arthroscope 400 will, perhaps, be best seen in reference to FIG. 9B. There it is seen that the image guide 32 extends through the needle 56 and through the cap 401 for exposure through aperture 464 at the base plate 402. Also, it is seen that the fiber bundle 122 extends through the needle 56 and through the cap 401 for exposure through aperture 406 at the base plate 402. As previously, disclosed the distal ends of both the image guide 32 and fiber bundle 122 are attached to the inside of the needle 56 at their respective distal ends. This attachment, though sufficient to hold these components together, does not extend through the length of the needle 56. Thus, the image guide 32 and fiber bundle 122 are freely positioned within the needle 56 through most of the length of the needle 56. This is so in order to help compensate for differences in the thermal expansion characteristics of the materials used in the manufacture of arthroscope 400.

Another structural feature of the arthroscope 400 which helps compensate for differences in thermal expansion characteristics, is the interaction between the neck 414 of cap 401 and the grommet 416. As best seen in FIG. 9B, a grommet 416 which is made of a relatively deformable material, such as an elastomeric material, surround the proximal end of needle 56 and is positioned between the needle 56 and the neck 414 portion of cap 401. The method for attaching the grommet 416 between the needle 56 and cap 401 can be accomplished by any means well known in the pertinent art.

The structural integrity of the components of arthroscope 400 is enhanced by filling the space within the cap 401 with an epoxy material. This is accomplished after the image guide 32 and fiber bundle 122 have been properly positioned within the needle 56 and have had their proximal ends respectively engaged for exposure through the apertures 404 and 406 on base plate 402. Consequently, the port 412, shown in FIG. 9A is provided for introducing an epoxy material into the cap 401 after the other components have been properly positioned.

As will be appreciated by the skilled artisan, it is important to the operation of the arthroscope 400 that it be optically aligned with camera assembly 202. Specifically, it must happen that image guide 32 be aligned with focusing optic 116 of the camera assembly 202, and that the fiber bundle 122 be aligned with the fiber 130. This, of course, is accomplished through the physical connection of the arthroscope 400 to the camera assembly 202. The optical effect, however, must be oriented with the physical apparatus so that the operator will know where he is looking with the arthroscope 400. For the arthroscope 400 this orientation is easily accomplished by providing visual means on the cap 401 to indicate the relationship between the image guide 32 and the orientation of the lens 48 at the distal end of the image guide 32. Specifically, the clip 410 is formed differently than the clip 408 so that the differences in their appearance can be used for orienting the arthroscope 400 during its operation.

OPERATION

In the operation of arthroscope 10, reference is initially made to FIGS. 1 and 2. Cannula assembly 68 with attached cannula 64 is detached from scope assembly 80. A trocar (not shown) is positioned through cannula 64, and the trocar is inserted into knee 14 to establish the entry site 12 for cannula 64. Once cannula 64 has been inserted into knee 14, the trocar can be removed from cannula 64. Disposable scope assembly 80 can then be attached to camera assembly 100, and camera assembly 100 placed in light communication with lamp 20. Also, camera assembly 100 is electrically connected to CCU 24. The disposable scope assembly and attached camera assembly 100 are inserted into cannula 64 to establish probe 30, and cannula assembly 68 is engaged with scope assembly 80.

When probe 30 has been inserted into knee 14 as disclosed and disposable scope assembly 80 has been attached to camera assembly 100, scope assembly 80 can be rotated clockwise and counterclockwise relative to camera assembly 100 to selectively focus the camera on the back of the image guide 32. More particularly, in reference to FIGS. 7 and 8, when scope assembly 80 is rotated relative to camera assembly 100, image guide 30 is rotated about its axis 44, as indicated by arrow 294. Recall that front tube 96 (and, hence, image guide 30) can be rotated ±170° relative to axis 44, so that the angle represented by arrow 294 in FIG. 8 is approximately 340°. Thus, image guide 30 can be rotated through 340°. As image guide 30 rotates, distal base 54 of GRIN lens 48 moves through a donut-shaped swath, and the viewing area 296 through which light can pass to enter distal base 54 moves through a relatively large region 298. Consequently, light from a relatively large region of knee 14 can enter distal base 54 of GRIN lens 48, and the image of this light processed by arthroscope 10 as described above for display on CRT 26 and recording by VCR 28. After the examination of patient 16, scope assembly 80 can be detached from camera assembly 100 and disposed of in a suitable receptacle, and a new scope assembly (not shown) engaged with camera assembly 100 for permitting the examination of another patient with arthrosccpe 10.

The operation of arthroscope 200 is in all essential respects identical to the operation of arthroscope 10, with the exception that cannula assembly 206 can rotate relative to scope assembly 204. Stated differently, scope assembly 204 can be rotated relative to cannula assembly 206, i.e., cannula assembly 206 can remain rotationally stationary with respect to the operator of arthroscope 200. By permitting cannula assembly 206 to remain stationary relative to the operator of arthroscope 200, fluid line 230 also remains stationary relative to the operator of arthroscope 200. Consequently, fluid line 230 will not become wrapped around cannula assembly 206 and will accordingly not unduly interfere with the operation of arthroscope 200.

The arthroscope 400 is, in all important respects, similar to the arthroscope 200. Like arthroscope 200, and arthroscope 10, the componentry of arthroscope 400 is simplified and it is manufactured with materials which permit disposal of the arthroscope 400 after it has been used.

While the particular arthroscope as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. An arthroscope for use with a video camera which comprises:

a cap having a base plate engageable with said camera;

a needle including a hollow tube, said needle having a proximal end mounted on said cap, and said needle having a distal end distanced from said cap;

an illuminating fiber extending through said tube of said needle, said illuminating fiber having a proximal end and a distal end, said proximal end of said illuminating fiber extending from said tube and through said cap for light communication through said base plate;

an image guide extending through said tube of said needle, said image guide having a proximal end and a distal end, said proximal end of said image guide extending from said tube and through said cap for light communication through said base plate;

a lens attached to said distal end of said image guide; and means for holding said lens, said distal end of said image guide and said distal end of said illuminating fiber at said distal end of said needle.

2. An arthroscope as recited in claim 1 wherein said lens is a gradient refractive index (GRIN) lens.

3. An arthroscope as recited in claim 1 wherein said image guide includes a plurality of pixels.

4. An arthroscope as recited in claim 1 further comprising a plurality of illuminating fibers.

5. An arthroscope as recited in claim 1 wherein said needle is substantially straight to establish a longitudinal axis for said needle and said distal end of said image guide is angled relative to said longitudinal axis.

6. An arthroscope as recited in claim 5 wherein said image guide comprises a plurality of optical fibers, each said optical fiber having a substantially circular cross section, and said optical fibers are bent at said distal end of said image guide to present a substantially circular cross section for attachment with said lens.

7. An arthroscope as recited in claim 1 wherein said cap is substantially hollow to define a cavity, with said illuminating fiber and said image guide extending through said cavity from said proximal end of said tube to said base plate.

8. An arthroscope as recited in claim 7 wherein said cavity is filled with an adhesive material.

9. An arthroscope as recited in claim 1 further comprising an elastomeric grommet, said grommet being mounted on said cap to surround a portion of said tube and position said grommet between said cap and said tube of said needle to eliminate thermal expansion problems.

10. An arthroscope as recited in claim 1 further comprising:
   a light source;
   means for engaging said arthroscope with said light source to position said light source in light communication with said illuminating fiber; and
   means for engaging said arthroscope with said video camera to position said camera in light communication with said image guide for generating a visual display signal with said video camera of an object illuminated by said light source through said illuminating fiber.

11. An arthroscope as recited in claim 10 wherein said proximal end of said image guide at said base plate is distanced from said proximal end of said illuminating fiber at said base plate.

12. An endoscope for providing a visual image of an object comprising:
   a cap having a base plate;
   a needle including a hollow tube, said needle having a proximal end mounted on said cap, and said needle having a distal end distanced from said cap;
   an illuminating fiber extending through said tube of said needle, said illuminating fiber having a proximal end and a distal end, said proximal end of said illuminating fiber extending from said tube and through said cap for light communication through said base plate;
   an image guide extending through said tube of said needle, said image guide having a proximal end and a distal end, said proximal end of said image guide extending from said tube and through said cap for light communication through said base plate;
   a lens attached to said distal end of said image guide; and
   means for holding said lens, said distal end of said image guide and said distal end of said illuminating fiber at said distal end of said needle.

13. An endoscope as recited in claim 12 further comprising:
   a light source;
   means for engaging said endoscope with said light source to position said light source in light communication with said illuminating fiber;
   a camera; and
   means for engaging said endoscope with said camera to position said camera in light communication with said image guide for providing said visual image with said camera of an object illuminated by said light source through said illuminating fiber.

14. An endoscope as recited in claim 13 wherein said proximal end of said image guide at said base plate is distanced from said proximal end of said illuminating fiber at said base plate.

15. An endoscope as recited in claim 12 wherein said image guide comprises a plurality of optical fibers, each said optical fiber having a substantially circular cross section, and wherein said optical fibers collectively present a substantially circular cross section for attachment with said lens.

16. An endoscope as recited in claim 12 wherein said lens is a gradient refractive index (GRIN) lens.

17. An endoscope as recited in claim 12 wherein said image guide includes a plurality of pixels.

18. An endoscope as recited in claim 12 further comprising a plurality of illuminating fibers.

19. An endoscope as recited in claim 12 wherein said cap is substantially hollow to define a cavity, with said illuminating fiber and said image guide extending through said cavity from said proximal end of said tube to said base plate.

20. An endoscope as recited in claim 19 wherein said cavity is filled with an adhesive material.

21. An endoscope as recited in claim 12 further comprising an elastomeric grommet, said grommet being mounted on said cap to surround a portion of said tube and position said grommet between said cap and said tube of said needle to eliminate thermal expansion problems.

* * * * *